US005535736A

United States Patent [19]

Jzaw

[11] Patent Number: 5,535,736

[45] Date of Patent: Jul. 16, 1996

[54] INFLATABLE MOUTHPIECE

[76] Inventor: Gwo-Shyong Jzaw, 20, Sublane 2, Lane 347, Hsin Ming Street, Yang Mei, Taoyuan, Taiwan

[21] Appl. No.: 494,068

[22] Filed: Jun. 23, 1995

[51] Int. Cl.$^6$ .................................................. A61M 16/22

[52] U.S. Cl. ................................ 128/202.26; 128/205.21; 128/206.17; 128/206.12; 128/206.28

[58] Field of Search ......................... 128/205.27, 205.28, 128/205.29, 206.23, 206.28, 206.26, 206.12, 202.26, 202.27, 202.28, 202.29, 203.11, 203.21, 205.21, 205.17, 206.17

[56] References Cited

U.S. PATENT DOCUMENTS 4,840,170 6/1989 Dahrendoof et al. .............. 128/202.26

*Primary Examiner*—Edgar S. Burr
*Assistant Examiner*—V. Srivastava
*Attorney, Agent, or Firm*—Bacon & Thomas

[57] ABSTRACT

An inflatable mouthpiece includes an outer cover, an air bladder, a filter, a turnable cover and a liquid container. The air bladder is disposed in a space defined between the outer cover and the turnable cover. The liquid container is placed inside the air bladder. Soda powder is sprinkled on the liquid container within the air bladder. The liquid container is fitted in to a hemispherical recess of the outer cover such that a part of the container wall projects in a space of the outer cover. When the turnable cover is turned in a set direction, a press plate of the turnable cover contacts and presses the liquid container to cause a citric acid therein to flow out to react with the soda powder for producing a carbon dioxide gas to quickly inflate the air bladder.

4 Claims, 5 Drawing Sheets

INFLATABLE MOUTHPIECE

BACKGROUND OF THE INVENTION (a) Field of the Invention

The present invention relates to a mouthpiece, and more particularly to mouthpiece having an air bladder and filter, the air bladder being capable of automatic inflation.

(b) Description of the Prior Art

Social and industrial development and progress have resulted in erection of numerous high-rise buildings, and petro-chemical products are usually employed in furnishing the buildings' interior. In case of fire, such petro-chemical furnishings catch fire easily and produce toxic fumes, which may cause death of many people within a short span of time. In view of the above, various kinds of mouthpieces capable of filtering toxic gases are developed. Generally, the simplest mouthpiece construction is to arrange filtration materials such as activated carbon in between two layers of cotton fabric. But in such kind of conventional mouthpiece, the edges of the mouthpieces are not in sealingly close contact with the face around the mouth and nose area, and besides, it is not very comfortable to use since the mouth and nose are in direct contact with the mouthpiece. A more professional kind of mouthpiece is molded from rubber material and can fit tightly on the user's face around the mouth and nose area, and it is equipped with a toxic gas filtration device at a front portion thereof. Although this kind of mouthpiece may achieve better effects, it is more costly and the overall size is rather big; therefore, it is not very common nor convenient in carrying.

SUMMARY OF THE INVENTION

It is a primary object of the present invention to provide a small-sized mouthpiece with optimum filtration effects so that the user may carry it with him/her anywhere and utilize it in case of fire to avoid inhaling toxic gases while running for his/her life within a critical short period of time. In the present invention, an inflatable air bladder is provided in between an outer cover and a turnable cover. When the user turns the turnable cover, a press plate of the turnable cover will contact and press a liquid container to release the citric acid liquid therein to react with soda powder sprinkled in the air bladder around the liquid container to produce carbon dioxide gas which speedily inflates the air bladder.

Another object of the present invention is to provide a mouthpiece consisting of an air bladder disposed between an outer cover and a turnable cover, in which the mouthpiece is configured to be compact for easy carrying within the pocket or purse.

BRIEF DESCRIPTION OF THE DRAWINGS

The foregoing and other features and advantages of the present invention will be more clearly understood from the following detailed description and the accompanying drawings, in which.

DETAILED DESCRIPTION OF THE PREFERRED EMBODIMENT

Figure 1:
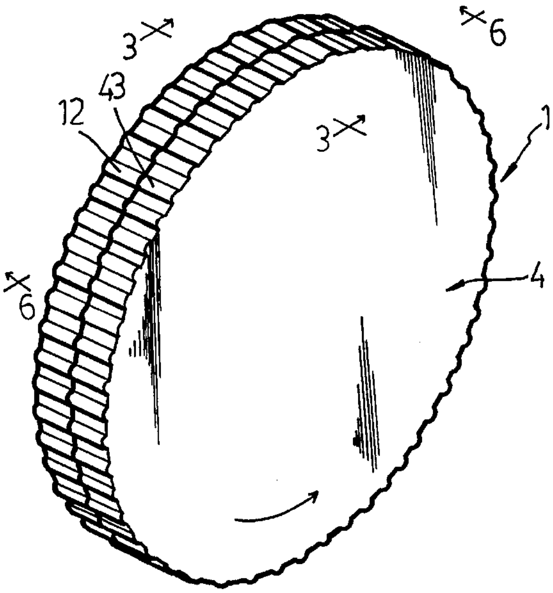
FIG. 1 is a perspective outer view of the present invention.
Figure 3:
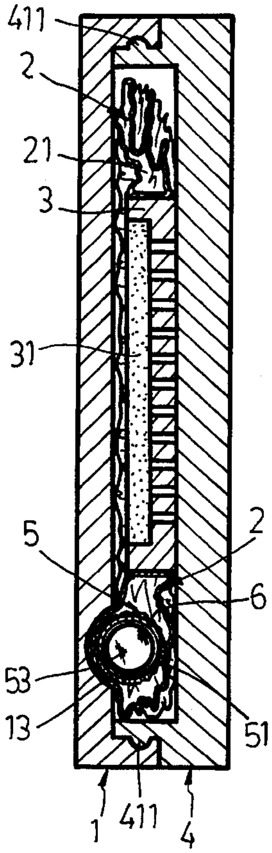
FIG. 3 is a sectional view taken along line 3—3 of FIG. 1.
Figure 2:
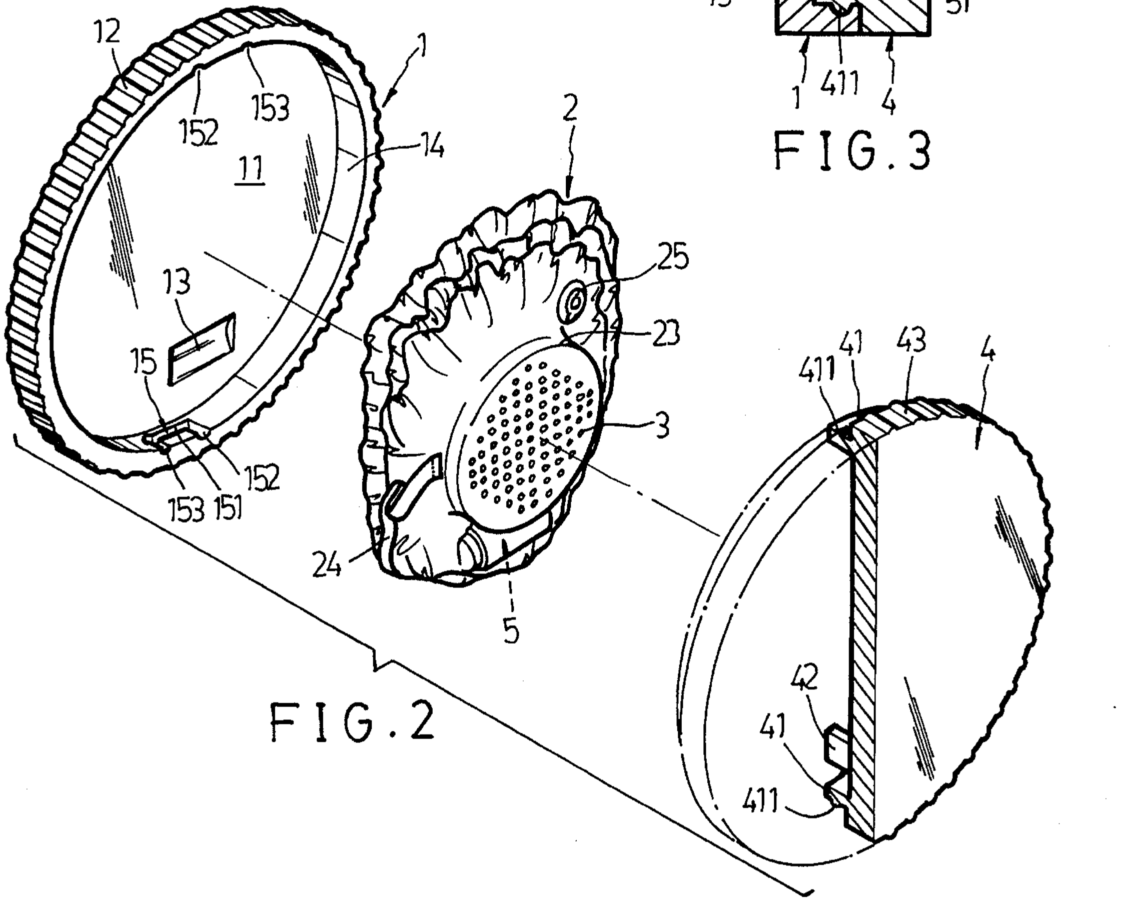
FIG. 2 is an exploded view of FIG. 1.
Figure 8:
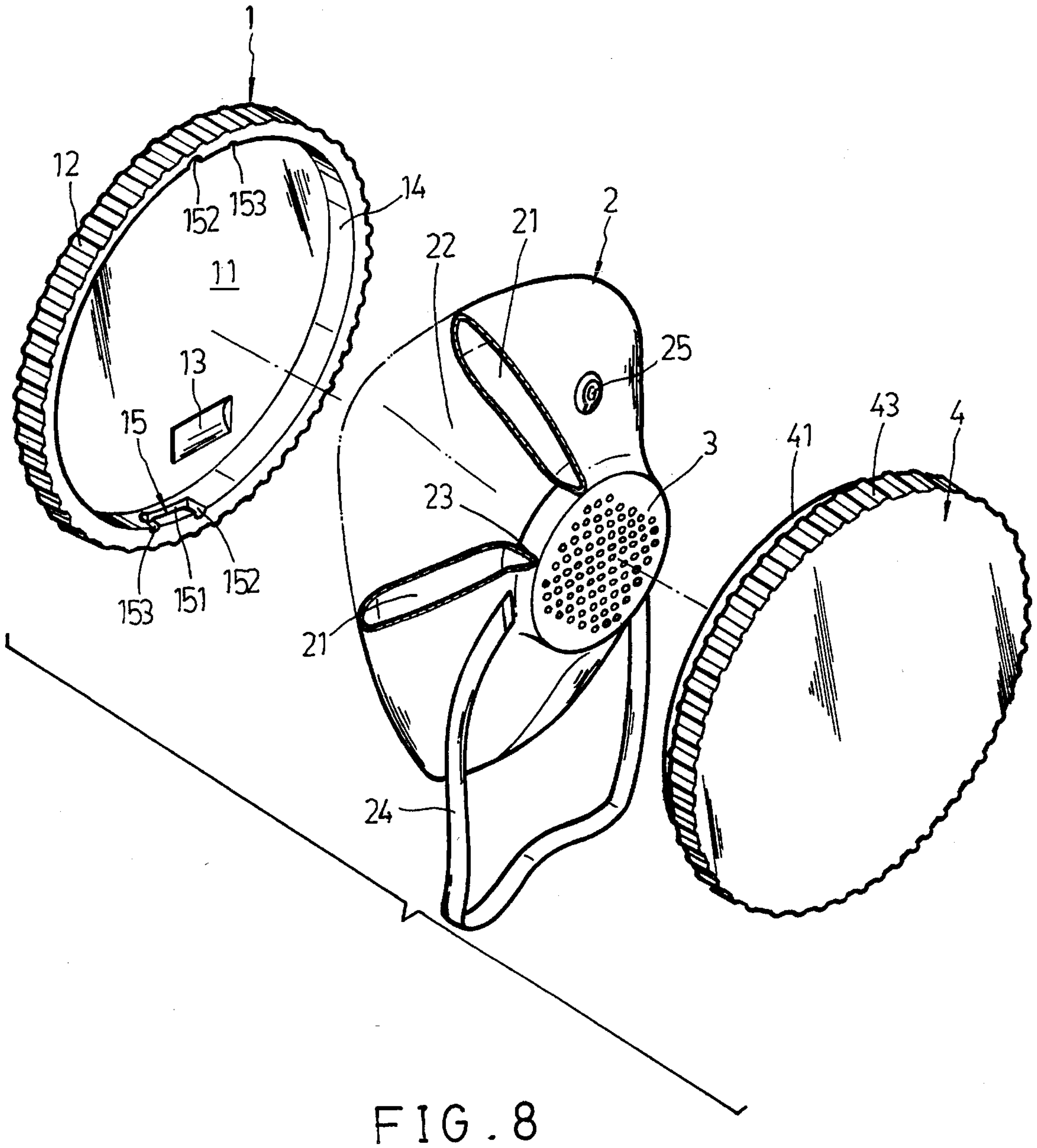
FIG. 8 is an exploded view of the present invention, showing the air bladder in an inflated state.

With reference to FIGS. 1 to 3, the mouthpiece according to the present invention essentially comprises an outer cover 1, an air bladder 2, a filter 3, a turnable cover 4 and a liquid container 5. The outer cover 1 is a circular disk structure with protruding teeth 12 around its circumference for easy grip. The outer cover 1 has an inner wall 11 with a horizontally disposed recess 13 at a set position. The recess 13 has a hemispherical curved cross section. Two guide slots means 15 are provided on opposite sides of an inner circumferential wall 14 of the outer cover 11. Each guide slot means 15 consists of a radial slot 151 and two axial slots 152, 153. Referring to FIGS. 2, 3 and 8, the above-mentioned air bladder 2 is formed of soft PVC film material, and two layers of PVC film material are adhered together by means of high frequency waves to define a space 21 therebetween. When the air bladder 2 is inflated (as shown in FIG. 8), a central portion thereof relatively form an axial hollow air path 22. Additionally, an open end 23 at a front section of the air path 22 is sealingly connected to a filter 3.

As shown in FIG. 3, the filter 3 has disposed therein filter material 31, such as activated carbon, for filtering toxic gases. A circumferential rim of the filter 3 is sealingly adhered to the open end 23 of the air bladder 2 so that the filter 3 may be located at one side of the air path 22.

With reference to FIGS. 3 to 6, the liquid container 5 is a cylindrical body having a diameter and length slightly smaller than those of the recess 13 of the outer cover 1. The liquid container 5 is pre-disposed in the space 21 of the air bladder 2 prior to union of the two layers of PVC film material. The liquid container 5 consists of a sleeve 51 having a multiplicity of pores in a circumferential wall thereof and an axially oriented spike 511 disposed at an inner bottom side thereof, and a piston 52 capable of being inserted within the sleeve 51, the piston 52 also having a spike 521 at one end thereof. The piston 52 is inserted with the end having the spike 521 into the sleeve 51 such that the other end thereof projects on the outside of the sleeve 51. A liquid packet 53 containing citric acid is disposed within the sleeve 51 prior to insertion of the piston 52 therein. The liquid packet 53 is wrapped in PE film or aluminum foil. When an external force is exerted on the piston 52, the spikes 511 and 521 at either ends of the liquid packet 53 will pierce therethrough so that the citric acid contained therein flows via the pores in the circumferential wall of the sleeve 51 to the outside of the liquid container 5.

Figure 9:
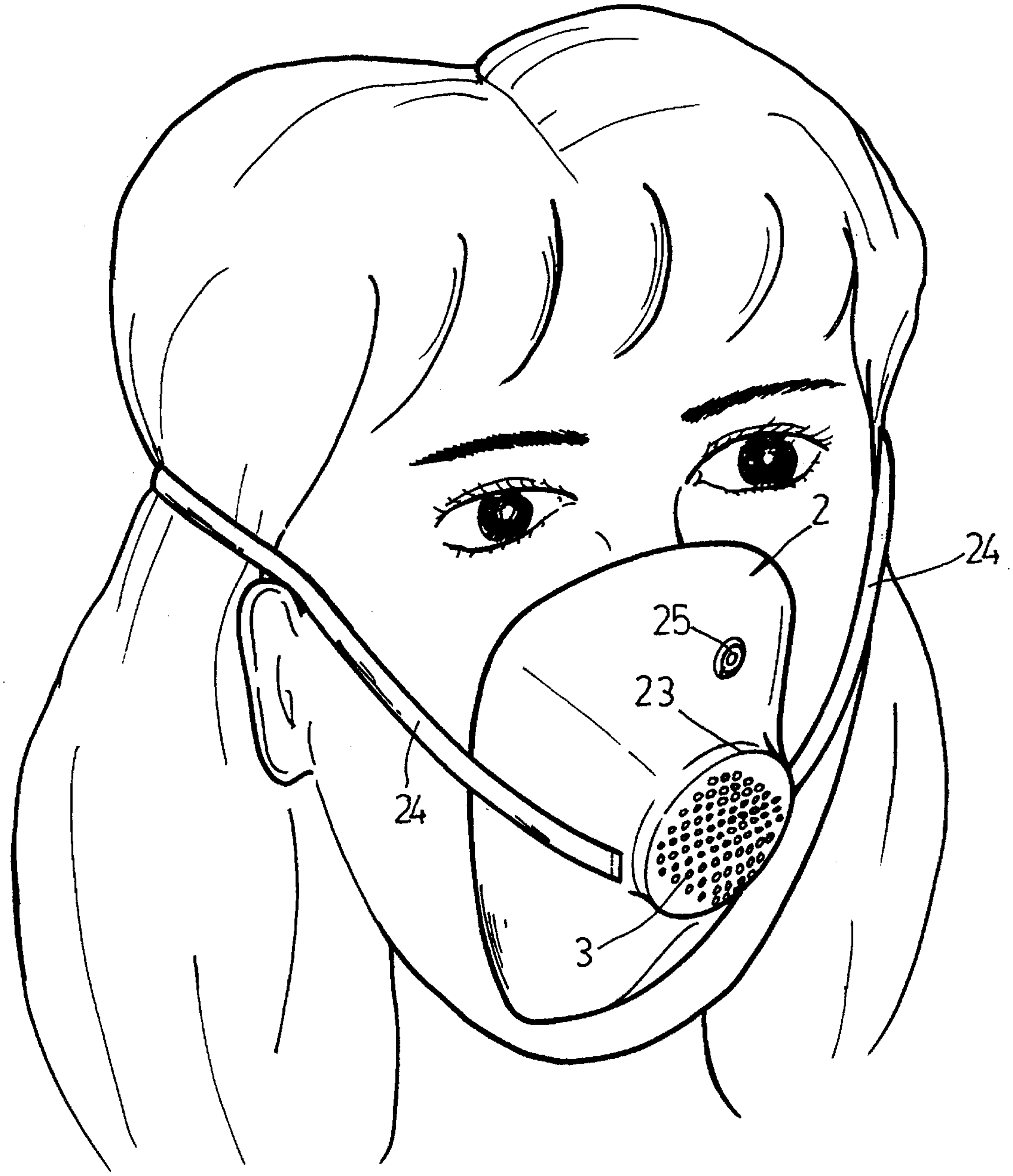
FIG. 9 is a perspective view of the present invention in a state of use.

When the liquid container 5 is placed within the air bladder 2, soda powder is sprinkled around the liquid container 5 before sealing of the air bladder 2. Therefore, when the citric acid flows out of the liquid container 5, it will react with the soda powder around the liquid container 5 to produce carbon dioxide gas, quickly inflating the space 21 in the air bladder 2. As shown in FIGS. 8 and 9, when the pressure of the carbon dioxide gas within the air bladder 2 is sufficient, the air bladder 2 will have a considerable rigidity. The user may then align a rear end of the air path 22 with his/her mouth and nose area and pull an elastic strap 24 around his/her head to properly position the mouthpiece of the invention on his/her face.

To ensure that the rear end of the air bladder 2 completely fits on the mouth and nose area of the user, in addition to providing a certain softness or suppleness for the air bladder 2 itself, the front end of the air path 22 may also be configured to have curvatures so that the rear end of the air bladder 2 may attach closely to the mouth and nose area of the user.

Figure 4:
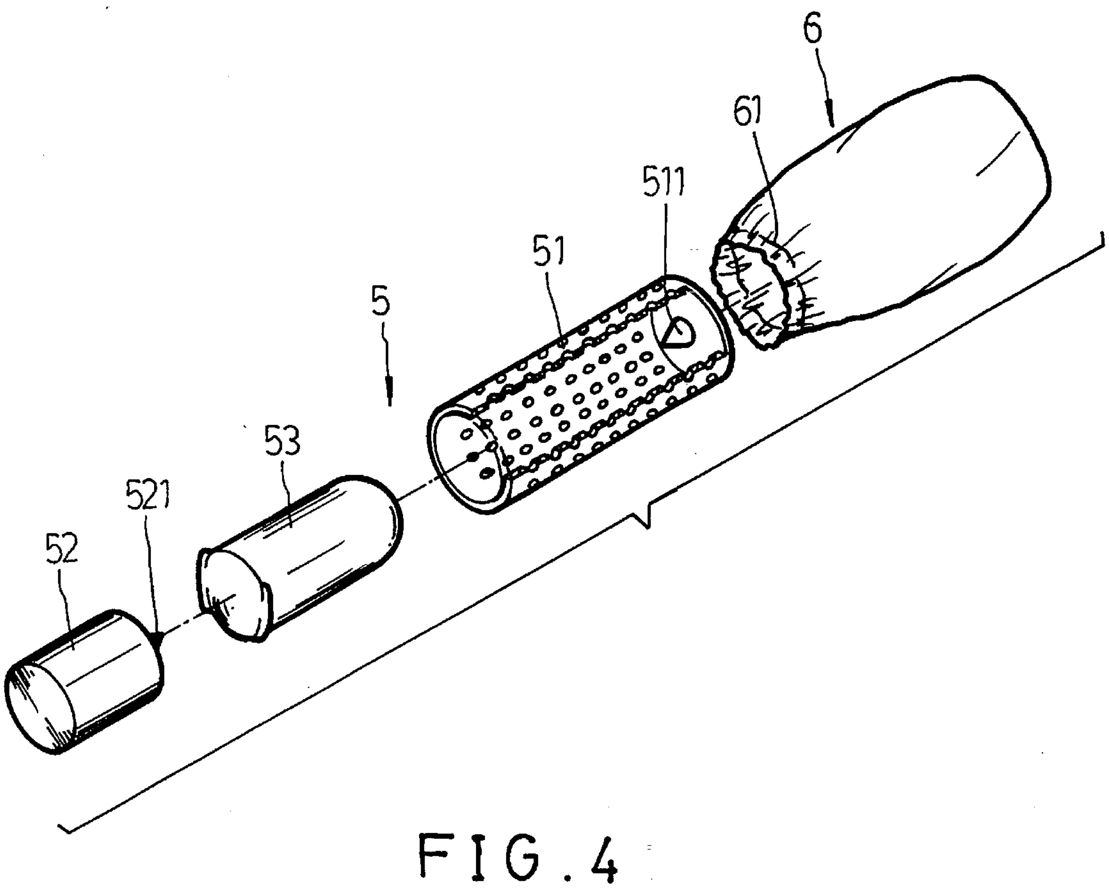
FIG. 4 is an exploded view of the liquid container according to the present invention.
Figure 5:
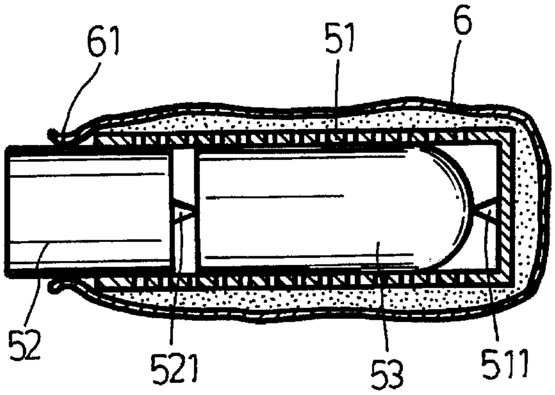
FIG. 5 is a sectional view of the liquid container according to the present invention.

It is described in the above preferred embodiment that a soda powder is spread around the liquid container 5 within the air bladder 2. But the soda powder may displace due to environmental factors so that the citric acid flowing out of the sleeve 51 to the outside of the liquid container 5 may not react with the soda powder or may not sufficiently react therewith. To prevent such occurrence, as shown in FIGS. 4 and 5, a bag 6 made of water absorbent and air permeable material, such as non-woven fabric or loosely knitted fabric, is used to hold the liquid container 5 and the soda powder, with an elastic band 61 wrapped around the outer surface of the liquid container 5. By such an arrangement, not only the movement of the soda powder is checked, but the bag 6 will also absorb the citric acid flowing out of the liquid container 5, so that the citric acid may react completely with the soda powder to produce adequate carbon dioxide gas to inflate the air bladder 2.

As the liquid container 5 is placed within the bag 6, the diameter of the curved recess 13 should be correspondingly modified to receive the liquid container 5.

As shown in FIGS. 2 and 3, when forming the air bladder 2, the air inside the space 21 of the air bladder 2 is drawn out so that the air bladder 2 becomes flat and foldable and may be accommodated within the space of the outer cover 1. Therefore, the liquid container 5 within the air bladder 2 may be fitted in the direction of the hemispherical recess 13 such that part of the liquid container 5 is accommodated therein.

Figure 6:
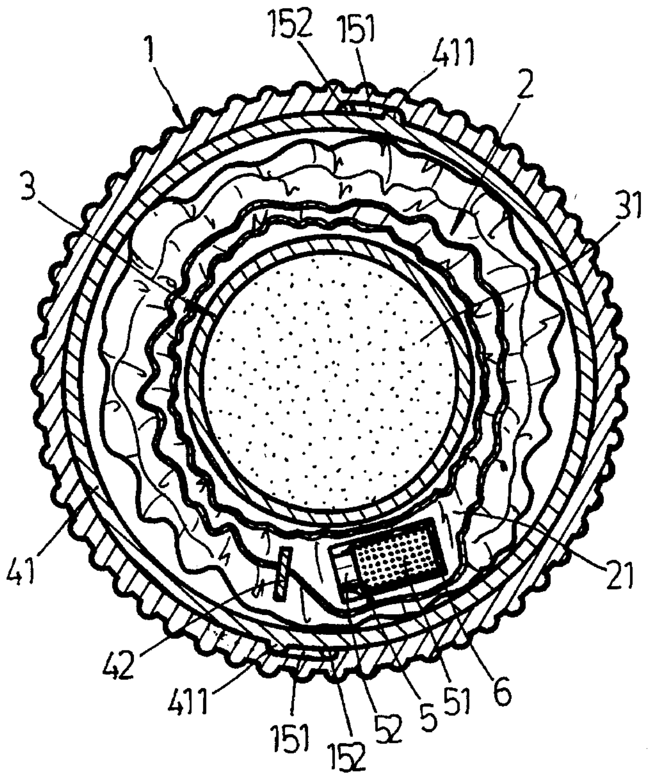
FIG. 6 is a sectional view taken along line 6—6 of FIG. 1.

As shown in FIGS. 2, 3 and 8, in addition to the protruding teeth 43, the turnable cover 4 is further provided with an insert rim 41 on an inner side thereof projecting in the direction of the outer cover 1, the insert rim 41 having an outer diameter equivalent to the inner diameter of the outer cover 1 so that the turnable cover 4 may be fitted onto the outer cover 1, and the air bladder 2 disposed in the outer cover 1 may be protected by the turnable cover 4. A press plate 42 is further provided on an inner wall of the turnable cover 4 at a position corresponding to that of the recess 13 of the outer cover 1 and projects near the inner wall 11 of the outer cover 1. Additionally, two retaining lugs 411 is provided on a circumferential rim of the insert rim 41 of the turnable cover 4 at positions corresponding to those of the axial slots 153 of the outer cover 1. When an external force is applied to the turnable cover 4, the retaining lugs 411 will fit into the corresponding radial slots 151 to unite the outer cover 1 and the turnable cover 4. As shown in FIG. 6, the position of the press plate 6 42 at this juncture is adjacent the liquid container 6.

Figure 7:
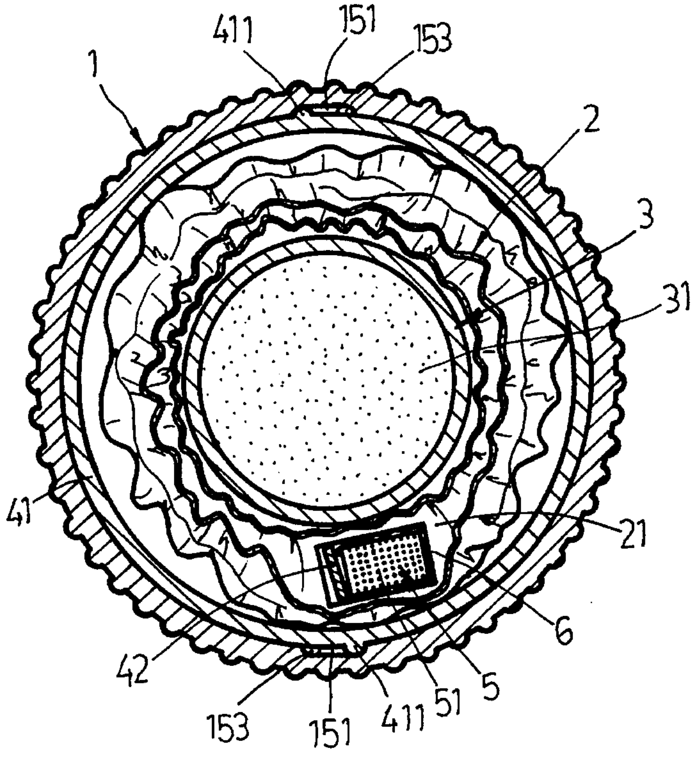
FIG. 7 is similar to FIG. 6, but showing the present invention in a state after the turnable cover is turned.

As shown in FIGS. 1 and 7, the turnable cover 4 is turned in the direction of the arrows so that each of the retaining lugs 411 slide along to the position of the corresponding axial slots 152, disengaging itself from the radial slot 151, so that the turnable cover 4 may be removed from the outer cover 1, and the air bladder 2 may also be taken out of the turnable cover 4. However, when the turnable cover 4 is turned the press plate 42 simultaneously moves towards the liquid container 6 to get into contact with and push the piston 52 (as shown in FIG. 5). As stated before, once the PVC film of the liquid packet is pierced, its citric acid content will flow out to the outside of the container 5 to produce carbon dioxide in the air bladder 2. as shown in FIG. 8. The mouthpiece of the present invention may then be put on the mouth and nose area as shown in FIG. 9.

In addition, as shown in FIG. 8, the air bladder 2 may be provided with a nozzle 25 for emergency use or repeated use of the air bladder 2.

Although the present invention has been illustrated and described with reference to the preferred embodiment thereof, it should be understood that it is in no way limited to the details of such embodiment but is capable of numerous modifications within the scope of the appended claims.

What is claimed is

1. An inflatable mouthpiece comprising an outer cover having a hemispherical recess, an air bladder, a filter, a turnable cover and a liquid container containing a citric acid solution, wherein said air bladder is disposed in a space defined between said outer cover and said turnable cover, said liquid container being disposed within said air bladder with soda powder sprinkled therearound; said bladder having an airpath, said filter being adhered to one side of said airpath of said air bladder; said liquid container being partially received in said hemispherical recess of said outer cover such that a part of the liquid container projects into said space, a press plate disposed near an inner wall of said outer cover at a position corresponding to that of said recess of said outer cover, said press plate pressing against said liquid container when an external force is exerted thereon to cause said citric acid solution within said liquid container to flow out therefrom and contact the soda powder around said liquid container, said turnable cover being disengageable from said outer cover after said turnable cover has been turned a predetermined amount.

2. An inflatable mouthpiece as claimed in claim 1, wherein said liquid container consists of a sleeve with a circumferential wall having a multiplicity of pores, said sleeve having an inner bottom side provided with a spike, and a piston for insertion into said sleeve, said piston having a spike at one end thereof, the end of said piston provided with the spike being inserted inside said turnable cover such that the other end thereof projects outside of said sleeve, said liquid packet containing citric acid solution being disposed within said sleeve.

3. An inflatable mouthpiece as claimed in claim 1, including two guide slot means consisting of a radial slot and two axial slots disposed on opposite sides of inner circumferential wall of said outer cover, said turnable cover being provided with two retaining lugs at positions corresponding to said axial slots of said outer cover such that said retaining lugs may each enter one of said axial slots and disengage from another axial slot upon closing of the turnable cover.

4. An inflatable mouthpiece as claimed in claim 1, wherein said liquid container and said soda powder are contained in a bag made of water absorbent material, said bag being fitted on an outer side of said liquid container.

* * * * *